United States Patent [19]

Hamprecht et al.

[11] Patent Number: 4,680,412

[45] Date of Patent: Jul. 14, 1987

[54] PREPARATION OF FLUOROPHTHALIMIDES

[75] Inventors: Gerhard Hamprecht, Weinheim; Juergen Varwig, Heidelberg; Wolfgang Rohr, Wachenheim, all of Fed. Rep. of Germany

[73] Assignee: BASF Aktiengesellschaft, Fed. Rep. of Germany

[21] Appl. No.: 615,806

[22] Filed: May 31, 1984

[30] Foreign Application Priority Data

Jun. 3, 1983 [DE] Fed. Rep. of Germany ....... 3320089

[51] Int. Cl.$^4$ .............................................. C07D 209/48
[52] U.S. Cl. .................................... 548/480; 548/473
[58] Field of Search ................................ 548/473, 480

[56] References Cited

U.S. PATENT DOCUMENTS

| | | | |
|---|---|---|---|
| 2,692,267 | 10/1954 | Campbell | 260/306.8 |
| 3,819,648 | 6/1974 | Boehme et al. | 548/480 |
| 4,092,300 | 5/1978 | Boldebuck | 525/424 |

FOREIGN PATENT DOCUMENTS

| | | | |
|---|---|---|---|
| 38852 | 11/1974 | Israel | 548/473 |
| 3068770 | 6/1978 | Japan | 548/545 |

OTHER PUBLICATIONS

Piutti, "Derivati Ureici e Tioureici Dell'acide Ftalico," Gazz Chim Italia., vol. XII, pp. 168–180, (1882).
Stern et al, "Cyclic Imides," Chem. Abst., 88: 120812(e), (1978).
Tanaka et al, "Isoqwinolinone Derivatives, " Chem. Abst. 88: 51971(s), (1978).
Zdrojek et al., "Studies on Phthalimide Synthesis," Chem. Abst., 91: 91314(y).
Nippon Mektron, "Manufacture of Poly(amide imide)," Chem. Abst. 98: 35164(g), (1982).
Lyman R. Caswell et al., "Dipole Moments of Some 3- and 4-Substituted Phthalimides and Phthalic Anhydrides Influence of Steric and Resonic Effects, *J. Org. Chem.*, 39 (1974), 1527–1531.

*Primary Examiner*—Donald G. Daus
*Assistant Examiner*—G. Hendricks
*Attorney, Agent, or Firm*—Keil & Weinkauf

[57] ABSTRACT

Fluorophthalimides are prepared by a process in which a fluorophthalic anhydride is reacted, in the presence of an aliphatic sulfone, with from 0.4 to 0.8 mole of urea per mole of fluorophthalic anhydride, and the reaction is carried out first at 110°–140° C. and then at 150°–170° C.

4 Claims, No Drawings

PREPARATION OF FLUOROPHTHALIMIDES

The present invention relates to a novel process for the preparation of fluorophthalimides by reacting the corresponding fluorophthalic anhydrides with urea in an aliphatic sulfone.

U.S. Pat. No. 2,692,267 discloses that substituted iminophthalimidines can be prepared by reacting the corresponding phthalic anhydrides with urea in the presence of ammonium molybdate or ammonium vanadate as a catalyst. According to J. Org. Chem. 39 (1974), 1527, 3-fluorophthalimide is obtained by heating a mixture of 1 mole of 3-fluorophthalic anhydride and 1.11 moles of urea in nitrobenzene at from 170° to 180° C. for 3 hours. This process gives a crude product which has to be purified by recrystallizing it twice from benzene and then subliming it under reduced pressure. The yield is 81%.

We have found that fluorophthalimides of the formula

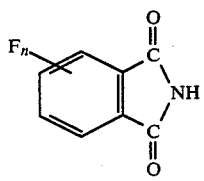

where n is 1 or 2, can be prepared much more advantageously by reacting a fluorophthalic anhydride of the formula

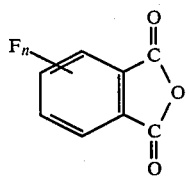

where n has the above meanings, with urea in the presence of a solvent at elevated temperatures, if from 0.4 to 0.8, preferably from 0.5 to 0.6, mole of urea is used per mole of fluorophthalic anhydride, an aliphatic sulfone is employed as the solvent, and the reaction is carried out first at 110°–140° C. and then at 150°–170° C.

Examples of fluorophthalic anhydrides of the formula II are 3-fluorophthalic anhydride, 4-fluorophthalic anhydride, 3,6-difluorophthalic anhydride, 4,5-difluorophthalic anhydride and 3,5-difluorophthalic anhydride.

Examples of aliphatic sulfones are the compounds of the formula

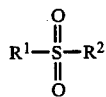

where $R^1$ and $R^2$ are identical or different and are each an aliphatic radical, preferably alkyl of 1 to 8, in particular 1 to 4, carbon atoms, or $R^1$ and $R^2$ together form an alkylene radical of 4 or 5 carbon atoms. Examples of suitable solvents of the stated type are dimethyl sulfone, diethyl sulfone, dipropyl sulfone, diisopropyl sulfone, dibutyl sulfone, diisobutyl sulfone, methyl ethyl sulfone, tetramethylene sulfone (=sulfolane) and pentamethylene sulfone, sulfolane being preferred. Advantageously, the solvent is used in an amount of from 50 to 1,000, preferably from 100 to 300, percent by weight, based on starting material II.

The reaction is carried out in two stages, the first stage being carried out at 110°–140° C., in particular 120°–135° C., and the second stage at 150°–170° C., in particular 160°–170° C. The first stage of the reaction is at an end when the evolution of gas is complete. This takes about 30–240 minutes. The second stage of the reaction is complete after about 10–20 minutes. The starting material II, the sulfone III and the urea can be mixed together in any sequence, in the stated temperature range. Advantageously, however, the starting material II is first mixed with the sulfone at 30°–40° C., after which the urea is added, while stirring, and the mixture is heated within the stated temperature range until evolution of gas is no longer observed. The procedure can be carried out under atmospheric or superatmospheric pressure, either continuously or batch-wise. The urea is used in an amount of, for example, from 0.4 to 0.8, preferably from 0.5 to 0.6, in particular from 0.51 to 0.55, mole per mole of starting material II. The procedure is carried out, for example, as follows: the urea is added to the mixture of the starting material II in the sulfone, and the mixture obtained by stirring is kept at the temperature required for the principal reaction for from 30 minutes to 4 hours, until the evolution of gas is complete, after which stirring is continued for a further 10–20 minutes at the temperature required for the subsequent reaction.

The fluorophthalimide is separated off from the reaction mixture in a conventional manner, for example by filtering, washing the solid and distilling the filtrate and washings.

In a particularly advantageous embodiment of the novel process, the fluorophthalic anhydride of the formula II is replaced by a reaction mixture obtained by treating the corresponding chlorophthalic anhydride with an acid chloride of sulfurous acid or of carbonic acid in the presence of an aliphatic sulfone, and then reacting the mixture with potassium fluoride. The corresponding chlorophthalic anhydride is the compound of the formula II in which F is replaced by Cl.

Reaction mixtures of the stated type are obtained, for example, when, in a first stage, the chlorophthalic anhydride is treated with an acid chloride of sulfurous acid or of carbonic acid at temperatures as high as 150° C. in the presence of an aliphatic sulfone, and, in a second stage, the treated mixture is then reacted with the potassium fluoride at from 150° to 250° C. For example, thionyl chloride or phosgene is used as the acid chloride of sulfurous acid or of carbonic acid, the amount of these used being, for example, from 1 to 20 percent by weight, based on the sulfone. Suitable aliphatic sulfones are compounds of the formula III, the sulfone being used in an amount of from 50 to 1,000 percent by weight, based on the chlorophthalic anhydride.

For example, the following procedure is advantageous: the chlorophthalic anhydride is stirred with the sulfone and, if appropriate, an N,N-disubstituted carboxamide as a catalyst, at from 30° to 40° C., the acid chloride is then added, and the mixture is advantageously heated to 50°–120° C., in particular 70°–100° C. The first stage is at an end when the evolution of gas is complete. Excess acid chloride can then be removed by, for example, blowing in an inert gas, such as nitrogen, or reducing the pressure. The potassium fluoride, and if appropriate a crown ether or cryptand as a catalyst, are then added, and the mixture is stirred for from 1 to 10 hours at from 150° to 250° C., in particular from 170° to 240° C., preferably from 190° to 220° C. The reaction mixture is then freed from inorganic residues by filtration under suction or distillation; when sulfolane is used as the solvent, it generally distils over together with the fluorophthalic anhydride of the formula II, boiling as it does within a similar range. The urea is then added to the resulting mixture which consists of the compound II and the sulfone and has been freed from inorganic residues, the mixture being stirred during the addition, and the reaction according to the invention is then carried out as described. However, it is also possible to add urea directly to the reaction mixture, and to carry out the reaction according to the invention without separating off inorganic by-products beforehand.

Suitable N,N-disubstituted carboxamides are those of 3 to 10 carbon atoms, e.g. N,N-dimethylformamide, N,N-dimethylacetamide, N,N-diethylformamide, N,N-di-n-propylacetamide, N-methyl-N-ethylformamide and N,N-diisopropylacetamide. The catalyst is advantageously used in an amount of from 0.2 to 2 percent by weight, based on the acid chloride. The crown ethers or cryptands are organic complex ligands which are very useful for bonding alkali metals. Crown ethers are cyclic neutral ethylene glycol ethers. The cryptands provide a three-dimensional cage. Regarding the preparation of these substances, reference may be made to "Kontakte" (1977), pages 11–31 and 36–48.

In comparison with the conventional processes, the process according to the invention gives a substantially better result in terms of the yield and purity of the fluorophthalimides. The fluorophthalic anhydrides used as starting materials do not have to be isolated, the overall reaction time is shorter, and purification processes involving recrystallization with organic solvents or sublimation can be dispensed with. Furthermore, the reaction mixture can be worked up more simply and reliably, particularly with regard to environmental protection, since there are no by-products apart from stoichiometric amounts of carbon dioxide. All these advantageous properties are surprising in view of the prior art.

The compounds which can be prepared by the process of the invention are useful starting materials for the preparation of crop protection agents, dyes and drugs. For example, they can be reacted with sodium hypochlorite under the conditions of a Hofmann degradation to give isomeric 3-fluoro- and 6-fluoroanthranilic acids; after the 3-fluoro derivative has been separated off, the product can be converted with benzoyl chloride, for example using the process described in German Pat. No. 2,914,915, to 5-fluoro-2-phenyl-4H-3,1-benzoxazin-4-one, which is used as a crop protection agent.

In the Examples which follow, parts are by weight.

EXAMPLE 1

A mixture of 49.8 parts (0.3 mole) of 3-fluorophthalic anhydride and 9.9 parts (0.165 mole) of urea in 126 parts of sulfolane is heated at 125°–130° C., while stirring. The mixture is stirred for 30 minutes, when the evolution of carbon dioxide is complete, after which stirring is continued for a further 15 minutes at 168° C. The solvent is distilled off (98 parts) at a bath temperature of 130°–160° C. under 0.3 mbar. A gas chromatogram shows that it contains 2.75 parts of 3-fluorophthalimide. The distillation residue is triturated with water, and the product is filtered off under suction, washed and dried, 44.5 parts of 3-fluorophthalimide of melting point 179°–182° C. being obtained. The total yield is 47.25 parts (95.3% of theory) of 3-fluorophthalimide.

EXAMPLE 2

500 parts (2.739 moles) of 3-chlorophthalic anhydride and 49.9 parts of thionyl chloride are added to 820 parts of sulfolane, while stirring. The mixture is stirred for 30 minutes at 100° C., after which the evolution of gas is complete. Excess thionyl chloride is stripped off under reduced pressure from a water pump, after which 175 parts of potassium fluoride are added and stirring is continued for 6 hours at 210° C. The mixture is cooled to 60° C., and 82 parts (1.37 moles) of urea are then added. The mixture is stirred for 1 hour 30 minutes at 130° C., when evolution of gas is complete, after which stirring is continued for a further 15 minutes at 170° C. The mixture is then cooled to room temperature, 300 parts of acetone are added, while stirring, and the predominantly inorganic precipitate is filtered off under suction. The filtrate is freed from acetone in a rotary evaporator, and the residue is then distilled over a 10 cm packed column at a bath temperature of 140°–170° C. under 0.4 mbar. The distillation residue is stirred with water, and the product is filtered off under suction, washed with methyl tert.-butyl ether and dried, 382 parts (84.5% of theory) of 3-fluorophthalimide of melting point 176°–179° C. being obtained. By treating the inorganic residue with 300 parts of acetone, separating off the extract and evaporating it down under reduced pressure, a further 29 parts (6.8% of theory) of 3-fluorophthalimide of melting point 166°–178° C. are isolated.

EXAMPLE 3

A stirred solution of 250 parts (1.369 moles) of 4-chlorophthalic anhydride in 450 parts of sulfolane is gassed with 50 parts of phosgene at 100° C. in the course of 40 minutes. Excess phosgene is stripped off under reduced pressure from a water pump, after with 95.4 parts of potassium fluoride are added at 80° C., and stirring is continued for 3 hours 30 minutes at 215° C. The reaction product and the sulfolane are then distilled off together at 115°–125° C. and under 0.3 mbar from the residue remaining behind. Finally, another 126 parts of sulfolane are added in order to carry out a further azeotropic distillation of 4-fluorophthalic anhydride which has not passed over. The resulting distillate (753 parts) contains 177 parts (78% of theory) of 4-fluorophthalic anhydride which is pure according to gas chromatography.

8.2 parts (0.137 mole) of urea are added to 185 parts of the distillate (containing 43.4 parts (0.261 mole) of 4-fluorophthalic anhydride). The mixture is stirred for 3 hours at 135°–140° C., after which the evolution of gas is complete, and is finally heated for a further 10 minutes at 160° C. The solvent is distilled off (144.2 parts) at 115°–130° C. and under 0.3 mbar. According to gas chromatography, it contains 9.6 parts of 4-fluorophthalimide. The distillation residue is stirred with water, and the product is filtered off under suction, washed and dried, 31 parts of 4-fluorophthalimide of melting point 174°–176° C. being obtained. The total yield is 40.6 parts (94.2% of theory) of 4-fluorophthalimide.

We claim:

1. A process for the preparation of a fluorophthalimide of the formula

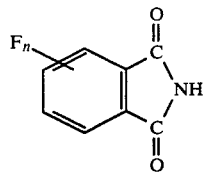

where n is 1 or 2, which comprises: reacting a fluorophthalic anhydride of the formula

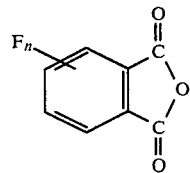

where n has the above meanings, with urea in the presence of a solvent at elevated temperatures, wherein from 0.4 to 0.8 mole of urea is used per mole of fluorophthalic anhydride, an aliphatic sulfone is employed as the solvent, and the reaction is carried out first at 110°–140° C. and then at 150°–170° C.

2. The process of claim 1, wherein the aliphatic sulfone is selected from the group consisting of dimethyl sulfone, diethyl sulfone, dipropyl sulfone, diisopropyl sulfone, dibutyl sulfone, diisobutyl sulfone, methyl ethyl sulfone, sulfolane and pentamethylene sulfone.

3. The process of claim 1, wherein the aliphatic sulfone is sulfolane.

4. The process of claim 1, wherein from 0.5 to 0.6 mole of urea is used per mole of fluorophthalic anhydride.

* * * * *